United States Patent [19]

Takematsu et al.

[11] 4,131,803
[45] Dec. 26, 1978

[54] APPARATUS FOR DETECTING DEFECTS IN SHEET MATERIAL

[75] Inventors: Shigeru Takematsu; Tohji Yoshida; Yukio Ikushima; Kunio Takeuchi, all of Takatsuki; Arao Kakinaka, Nishinomiya; Koichi Matsunaga, Neyagawa; Mamoru Shimakura, Takatsuki; Yoji Komura, Takatsuki, all of Japan

[73] Assignees: Toyo Boseki Kabushiki Kaisha; Kasuga Denki Co., Ltd., both of Japan

[21] Appl. No.: 738,151

[22] Filed: Nov. 2, 1976

[30] Foreign Application Priority Data

Nov. 5, 1975 [JP] Japan ............................. 50/133423
Jul. 24, 1976 [JP] Japan ............................. 51/99148
Jul. 24, 1976 [JP] Japan ............................. 51/99149

[51] Int. Cl.² ............................................. G01N 21/32
[52] U.S. Cl. ..................................... 250/563; 250/572; 356/431
[58] Field of Search ................. 250/562, 563, 572, 200

[56] References Cited

U.S. PATENT DOCUMENTS

| 3,308,658 | 3/1967 | Bryan | 250/563 X |
|---|---|---|---|
| 3,385,971 | 5/1968 | Fertig et al | 250/572 |
| 3,558,900 | 1/1971 | Moskowitz | 250/562 |
| 3,840,302 | 10/1974 | Brunton et al. | 250/563 X |
| 3,909,138 | 9/1975 | George et al. | 250/563 X |

Primary Examiner—Palmer C. Demeo
Attorney, Agent, or Firm—Staas & Halsey

[57] ABSTRACT

An apparatus for detecting a defect in a sheet like material, comprising: a photodetector provided opposite to a textile sheet in the vicinity of the weaving line of a weaving machine, and a prime mover for slidably driving said photodetector in the lateral direction throughout the width of the weaved textile sheet, characterized in that normally the said prime mover is adapted to convert the moving direction whenever the photodetector reaches either side edge of the weaved textile sheet but is further adapted to reverse the moving direction whenever the photodetector detects a defect in the weaved textile sheet, whereby said photodetector is caused to detect repeatedly the same defect and the weaving machine is controlled to stop the weaving operation whenever the photodetector detects the same defect more times than a predetermined number of times.

8 Claims, 14 Drawing Figures

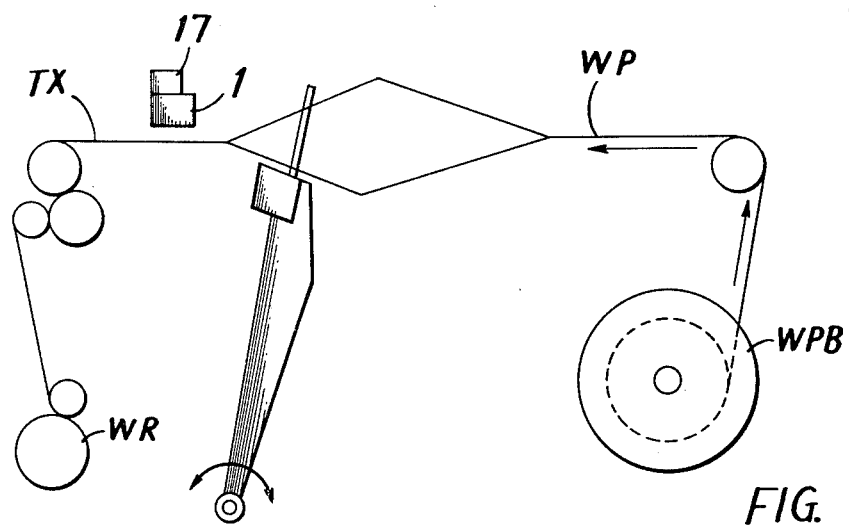
FIG. 1
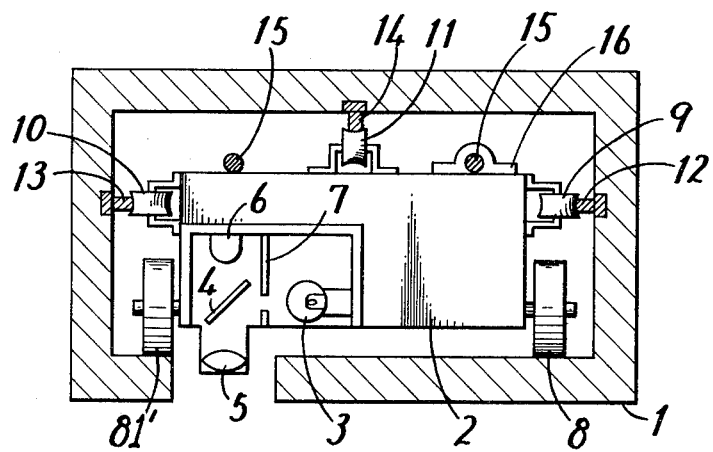
FIG. 2A
FIG. 2B
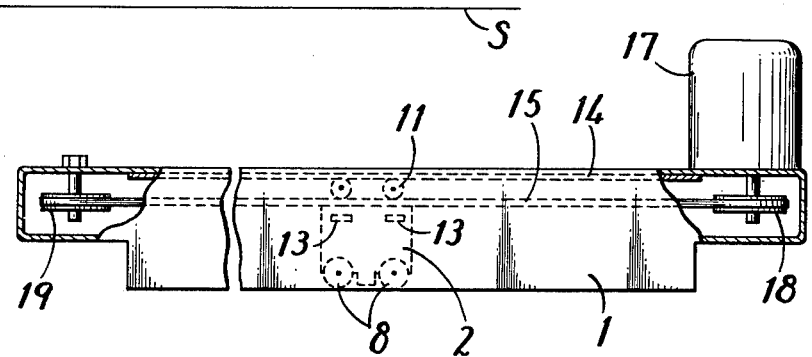

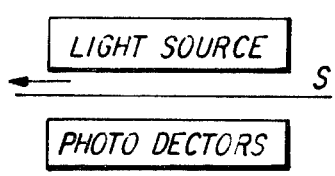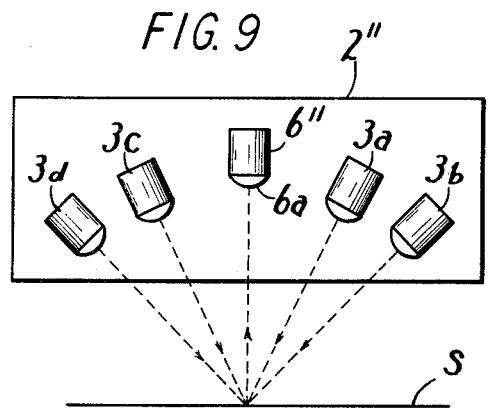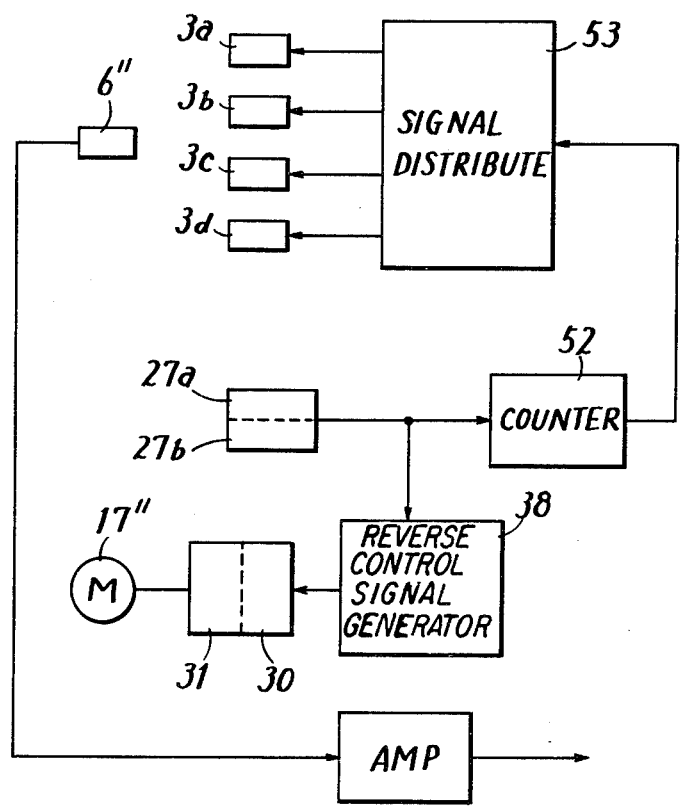

APPARATUS FOR DETECTING DEFECTS IN SHEET MATERIAL

BACKGROUND OF THE INVENTION

1. Field of the Invention

The present invention relates to an apparatus for detecting a defect in a sheet like material. More specifically, the present invention relates to an improvement in such a defect detecting apparatus adapted for detecting in a photoelectric manner a defect in a sheet like material while it is transferred during a weaving operation, such as through a sheet processing step, and the like.

2. Description of the Prior Art

In a weaving operation, for example, a defect such as a weaving flaw could occur in a weaved textile, because of a poor quality of a raw yarn, poor sizing, improper adjustment or maintenance of a weaving machine, and the like. Conventionally, therefore, it has been a common practice in the art that a defect in the weaved textile is detected during a weaving process or a testing process for the purpose of quality control of the weaved textile and for the purpose of enhancement of reliability to the product. Of late, various automatic or mechanical defect detecting apparatus and methods have been proposed and put in practical use. A typical automatic defect detection employs a photoelectric detection by the use of a light source and a photodetector provided relative to a textile sheet to be tested. One type of such photoelectric defect detecting system comprises a plurality of photodetectors arranged in the lateral direction of the textile sheet throughout the width of the textile sheet, wherein the photodetectors are fixedly provided, while the textile sheet is adapted to travel in the longitudinal direction. In view of the fixed provision of the photodetectors, this type may be referred to as "a fixed type". Another type of such photoelectric defect detecting system comprises a light source and a photodetector provided relative to a textile sheet, either or both of which is adapted to scan the textile sheet in the width direction. Hence, this type may be referred to as "a scanning type". The photoelectric defect detecting system of the so called scanning type can be classified into (1) an optical scanning type comprising a mirror rotatably provided to provide a scanning light beam in the width direction and (2) a mechanical scanning type comprising a detector provided to scan mechanically the textile sheet in the width direction. A fixed type defect detecting system is expensive in cost because a multiplicity of photodetectors are provided arranged in the lateral direction throughout the width of the textile sheet, which requires a complicated electrical circuit configuration. On the other hand, a defect detecting system of an optical scanning type requires a precise optical system, which also makes the system complicated and expensive in cost. By contrast, a defect detecting system of a mechanical scanning type can be simplified in structure and is more practical. Hence, it has been advantageously utilized as a defect detecting apparatus for a tricot knitting machine. Nevertheless, a mechanical scanning type defect detecting apparatus is disadvantageous in that it is of a slow scanning speed as compared with an optical scanning type apparatus. Hence, in the case of a sheet being tested of a wider width, it takes more time for a detector to again detect the same defect which was detected in the previous scanning cycle, with the result that it becomes impossible to determine whether the detected defect is a continuous one or separate ones.

As described previously, various types of defects could occur during a weaving process for various reasons. Particularly, a defect extending in the warp direction could be caused in the case where a warp defect preventing apparatus is not properly operated because the warp is snapped or loosened and is twisted with the peripheral portion of the warp sheet, and the like. A warp directional defect could be a relatively large continuous defect. Hence, it is desired that this type of warp directional continuous defect be detected as early as possible, thereby to avoid degradation of quality of the product in a weaving process.

SUMMARY OF THE INVENTION

A principal object of the present invention is to provide an apparatus for detecting defect in sheet like material, which is simple in structure and is inexpensive in cost.

Another object of the present invention is to provide an apparatus for detecting defect in sheet like material which is adapted to detect the magnitude of a defect for avoiding a continuous defect larger than a selected minimum size.

A further object of the present invention is to provide an apparatus for detecting a defect in sheet like material which is adapted to set the size of a possible detectable minimum defect.

Still a further object of the present invention is to provide an apparatus for detecting a defect of sheet like material, which is capable of positively detecting an abnormality in a variety of shapes and sizes.

A further object of the present invention is to provide an apparatus for detecting a defect in sheet like material which is easy in operation, less liable to cause noise and is capable of processing a detected signal with reliability.

Briefly described, the present invention comprises an apparatus for detecting a defect in sheet like material, comprising: defect detecting means provided movably in the width direction relative to said sheet like material, means for moving at least either one of said sheet like material and said defect detecting means, and means responsive to detection of a defect by means of said defect detecting means for controlling said moving means to restrict said relative movement within a predetermined small width spanning said defect.

These objects and other objects, features, aspects and advantages of the present invention will become more apparent from the following detailed description of the invention made with reference to the accompanying drawings.

BRIEF DESCRIPTION OF THE DRAWINGS

FIG. 1 is a simplified side view of a weaving machine employing the present invention;

FIG. 2A is a plan view showing a preferred embodiment of a scanning frame 1 for use in the present invention;

FIG. 2B is an elevational view of the FIG. 2A embodiment;

FIG. 9 is a diagrammatic view of a further preferred embodiment of the detecting apparatus 2 of the present invention; and FIG. 10 is a block diagram of a control circuit of the inventive detecting apparatus.

FIG. 11 is a block diagram showing light beam transmission through the textile sheet.

Figure 3:
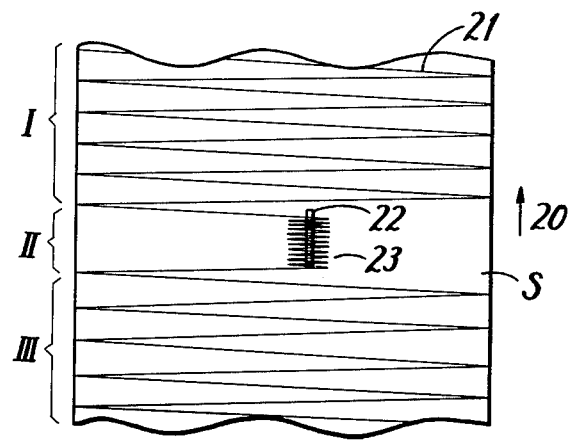
FIG. 3 is an illustration showing a scanning locus by the head for the purpose of defect detection in accordance with the present invention.

DESCRIPTION OF THE PREFERRED EMBODIMENT:

Referring first to FIG. 1, a textile TX is woven by supplying the warp WP in sheet fashion from a warp supply beam WPB, shedding the warp sheet and inserting the woof, and wound upon a winding roll WR, as is well known to those skilled in the art. A scanning frame 1 is provided opposite to the woven textile sheet in front of the weaving line of the weaving machine, as shown in the figure, for the purpose of detecting as soon as a flaw or defect occurs during the weaving operation, as to be more fully described subsequently.

Referring now to FIGS. 2A and 2B, the scanning frame 1 is described in detail. It should be pointed out that the embodiment shown comprises a detecting head of the coaxial reflection type. The scanning frame 1 is internally provided with a detecting device 2 comprising a detecting head and an amplifier for amplifying the output signal from the detecting head. The detecting device 2 is provided so as to scan a textile sheet S and arranged so as to be moved or traversed in the width direction of the textile sheet S which is supplied or made to travel longitudinally with respect to the scanning frame 1. The detecting head comprises a lamp 3 serving as a light source, a slit plate 7 having a slit, a half mirror 4, a lens 5 and a photodetector 6, as arranged as shown in the figure. The light beam from the lamp 3 is trimmed to a desired shape of light beam by means of the slit in the slit plate 7. In the embodiment shown, for the purpose of easily detecting only a warp directional defect, the sectional shape of the light beam to be made to impinge on the textile sheet is selected to be elongated in the warp direction. The light beam emitted from the lamp 3 through the slit in the slit plate 7 is reflected from the half mirror 4 and focused by means of the lens 5 and then made to impinge on the surface of the textile sheet S. The light beam reflected from the surface of the textile sheet S is transmitted back along the same light beam path and through the half mirror 4 to impinge on the photodetector 6. Accordingly, if and when an abnormality exists on the textile sheet S where the light beam is being reflected, the intensity of the light beam so reflected from the sheet S and received by the photodetector 6 will vary accordingly. The output from the photodetector 6 is amplified by an amplifier (not shown) in the detecting device 2 and produces a defect detection signal.

The detecting device 2 is provided with rollers 8 and 81' for stabilized traveling along the scanning frame 1, such that the detecting device 2 is movably supported so as to run along the scanning frame 1 in the width direction of the woven textile sheet. Supporting contact rollers 9, 10 and 11 are also provided on the detecting device 2 in an electrically isolated manner therefrom, and the contact rollers 9, 10 and 11 are engaged with guide rails 12, 13 and 14, respectively, mounted on the scanning frame 1 also in an electrically isolated manner therefrom. These contact rollers are mounted so as to roll on the guide rails, while these contact rollers 9, 10 and 11 are also electrically connected to a power source terminal, a signal output terminal, and a ground terminal of the amplifier provided internally of the detecting device 2. A wire 15 in the form of a loop is provided to move to and fro between a driving pulley 18 and a driven pulley 19 which are rotated by means of a driving motor 17, as shown in FIG. 2B. The ends of the wire 15 are fixed to the detecting device 2 at fixing plate 16 thereon. As a result the detecting device 2 is moved to and fro for the purpose of scanning in the left and right direction when viewed along the longitudinal plane of the textile sheet. Limit switches are provided at the left and right extremity ends of the scanning frame 1, such that these limit switches are actuated whenever the detecting device 2 comes to the left and right extremity ends of the scanning width so as to determine the scanning width. These limit switches are utilized to reverse the rotation of the motor 17 to cause repetitive reciprocating scanning of the detecting device 2 in the left and right directions across the sheet width. The above described limit switches are preferably supported so as to be adjustably movable in the scanning width direction, so that the scanning width by the detecting device 2, i.e. the head, can be selected as desired.

Now referring to FIG. 3 as well as FIGS. 1, 2A and 2B, an example of a defect detecting operation in accordance with the present invention will be described. Referring to FIG. 3, the textile sheet S is transferred in the direction of an arrow 20. Let it be assumed the textile sheet 20 includes no defect in regions I and III but includes a defect 22 in a region II which extends longitudinally in the warp direction. According to the present invention, the scanning operation is carried out in the no defect region I throughout the full width of the textile sheet S to draw or describe a locus 21, but whenever a warp directional defect 22 is detected in the region II, a defect detected signal is produced from the above described contact roller 10 through the guide rail 13 to an external control circuit (not shown), which generates a motor reverse rotation signal to enable an appropriate relay. More specifically, the defect 22 is detected, the motor 17 is rotated in the reverse direction in response to the defect detected signal, thereby to make the detecting device 2 move in the reverse direction for the purpose of scanning. When the same defect 22 is detected in the reverse direction scanning operation, a similar operation is repeated, with the result that fractionally repetitive back and forth scanning operations take place for as long as the warp directional defect 22 exists and is detected, with the result that the fractionally repetitive scanning locus indicated by the reference numeral 23 in FIG. 3 is created by the scanning operation. When the region III is reached where the defect 22 disappears, no defect detected signal is produced any more and the normal full width scanning operation again is regained as effected in the region I, with the result that the scanning locus as shown as the reference numeral 21 is figured by means of the detecting device 2.

On the other hand, the external control circuit is structured such that it stores a multiple number of defect detected signals obtained during the above described fractionally repetitive back and forth scanning operation as shown as the numeral 23 and a control signal is generated only after a predetermined number of the defect detected signals occur which exceed an amount which has been preselected as adversely affecting the quality of the textile product. The above described control signal may be used to display or record the existence of a defect and/or to stop the operation of the weaving meachine.

Now referring to FIG. 4, another example of a defect detecting operation will be described. The FIG. 4 embodiment is a modification of the FIG. 3 embodiment and is aimed to prevent an undesired confusing control signal, such as a noise, from being obtained during the normal full width scanning operation which could be confused with a defect detected signal in spite of no defect in the textile sheet. More specifically, the FIG. 4 embodiment has been adapted such that whenever a defect detected signal is produced just once during the full width scanning operation, immediately thereafter one cycle of the fractionally repetitive back and forth scanning operation is effected for the purpose of reconfirmation of the defect detection, and thereafter the normal full width scanning operation is regained, with the result that first and second reconfirmative defect detections are made by the above described one cycle fractionally repetitive back and forth scanning operation as compared with the normal full width scanning operation. As a result, the existence of a defect can be detected with higher accuracy.

Figure 4:
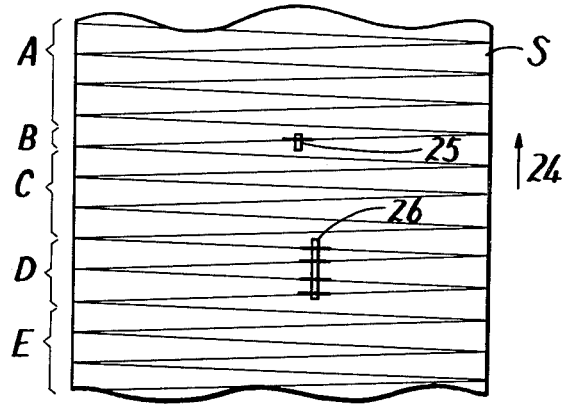
FIG. 4 is similar to FIG. 3 but shows an illustration of a scanning locus of the head of another example of defect detecting operation in accordance with the present invention.

Referring to FIG. 4, let it be assumed that the textile sheet is traveling in the direction of the arrow 24 and defects exist in the regions B and D while no defect exists in the regions A, C and E. When the scanning operation is shifted from the region A to the region B, the defect 25 is detected and only one cycle of the fractional back and forth scanning operation is effected by the detecting device 2 in response to the defect detected signal, as shown in the figure. Since the defect in the region B is too short in the warp direction, one cycle of the fractional back and forth scanning operation does not occur in the following normal full width scanning operation in the reverse direction, as seen in FIG. 4. By contrast, the defect 26 in the region D is long in the warp direction. Therefore one cycle of fractional back and forth scanning operation is effected for each normal full width scanning operation, insofar as the defect 26 is detected in the normal full width scanning operation, as seen in FIG. 4.

Figure 5:
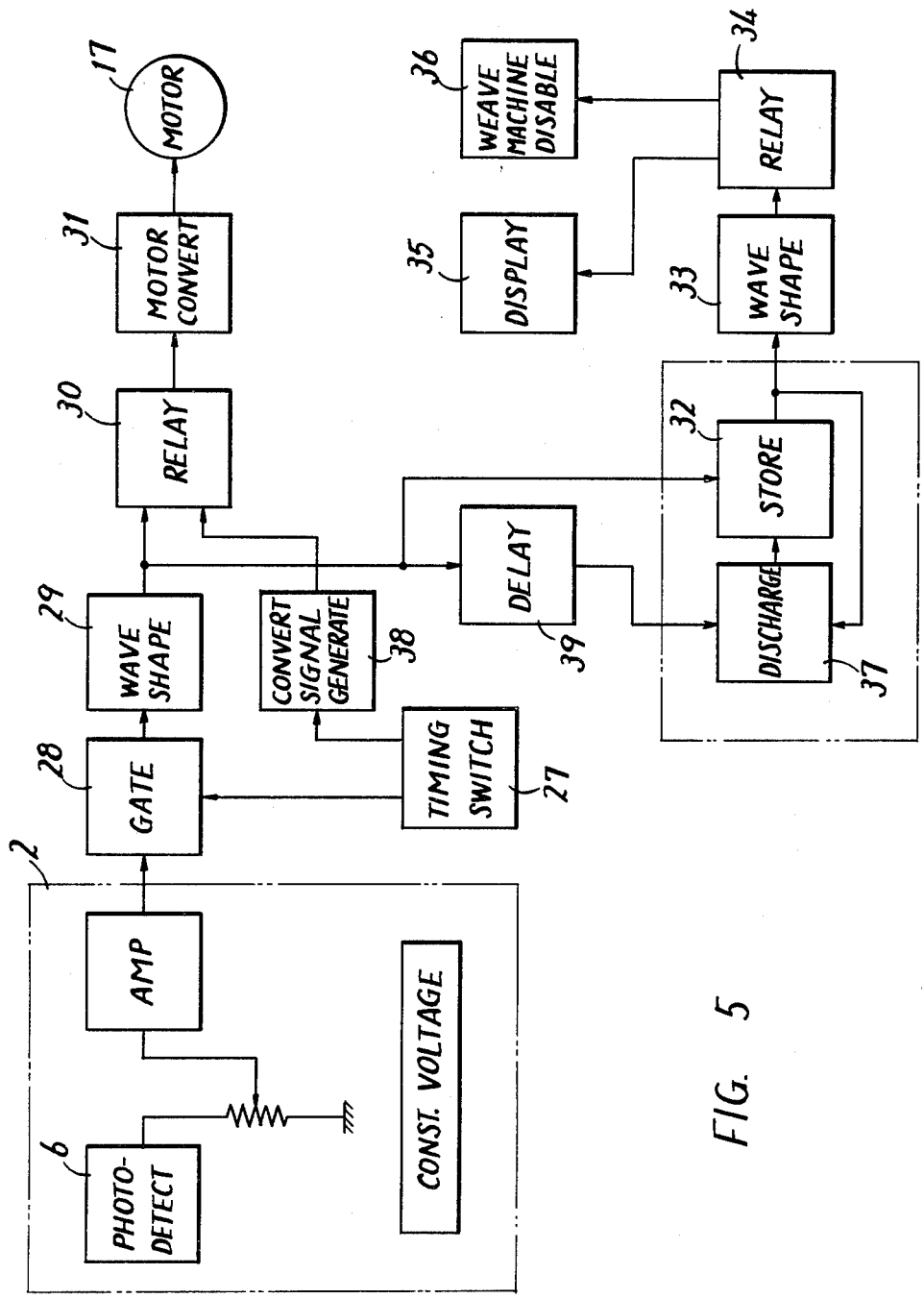
FIG. 5 is a block diagram of a preferred embodiment of the inventive apparatus.

FIG. 5 is a block diagram of a preferred embodiment of the inventive apparatus for performing the above described operation. Referring to FIG. 5, the output from the photodetector 6 in the detecting device 2 is applied through a variable resistor to an amplifier, so that the output signal from the photodetector 6, as properly adjusted in level, is amplified by the amplifier. The output from the amplifier is then applied to a gate circuit 28. The detecting device 2 may comprise a constant voltage source.

The gate circuit 28 is structured so that it is on/off controllable as a function of the timing signal obtainable from a timing switch 27 provided in association with the width direction of the textile sheet S, so that the defect detection signal from the detecting device 2 is allowed to pass through the gate 28 while it is controlled on. The defect detection signal passed by the gate circuit 28 is applied to a wave shaping circuit 29 comprising a monostable multivibrator, for example, wherein a pulse signal having a predetermined pulse width and amplitude is generated responsive to the above described defect detected signal. The output from the wave shaping circuit 29 is applied to a relay 30 and is also applied to a delay circuit 39 and a storage circuit 32. The delay circuit 39 is structured such that it is responsive to the above described pulse signal to provide an output signal after a delay of 30 seconds which is preferably adjustable as desired. The output from the delay circuit 39 is applied to a discharge circuit 37. The storage circuit 32 may comprise a charge storing means such as a capacitor C3 which stores an electric charge upon receipt of a pulse signal associated with the defect detected signal obtained from the wave shaping circuit 29. The storage circuit 32 is further structured such that whenever the potential of the stored charge reaches a predetermined level, which has been selected to a level commensurate with the eight consecutive defect detected signals in the embodiment shown, a level detected output is produced. The output from the store circuit 32 is applied to a wave shaping circuit 33 which may comprise a monostable multivibrator, and the output thereof applied to the above described discharge circuit 37. The discharge circuit 37 is structured such that upon receipt of the output from the delay circuit 39, or the output from multivibrator 33 as triggered from the storage circuit 32, any stored charge on C3 in the store circuit 32 is discharged thereby.

The pulse signal obtained from the pulse shaping circuit 33 when the potential of the charge stored in the store circuit 32 reaches a predetermined level is applied to a relay circuit 34. The relay circuit 34 is responsive to the output from the wave shaping circuit 33 to energize a display 39 and to provide a weaving machine disabling signal to a weaving machine stop control circuit 36.

The above described timing switch 27 is structured such that it enables a reverse control signal circuit 38 if and when the detecting device reaches the opposite extremities in the width direction of the textile sheet or the predetermined positions in the vicinity of the opposite ends for defining a predetermined width in the width direction of the textile sheet. Accordingly, the reverse control signal circuit 38 is responsive to the timing switch 27 when the detecting device 2 reaches the opposite extremities to provide a motor reverse signal, which is applied to the above described relay circuit 30. The relay circuit 30 becomes operable responsive to the output from the wave shaping circuit 29 associated with the defect detected signal, or the reverse signal from the reverse control signal circuit 38 to enable the motor reverse control circuit 31. The motor reverse control circuit 31 controls the motor 17 so as to be rotated in the reverse direction so that the detecting head in the detecting device 2 scans the textile sheet in the reverse direction.

Figure 6:
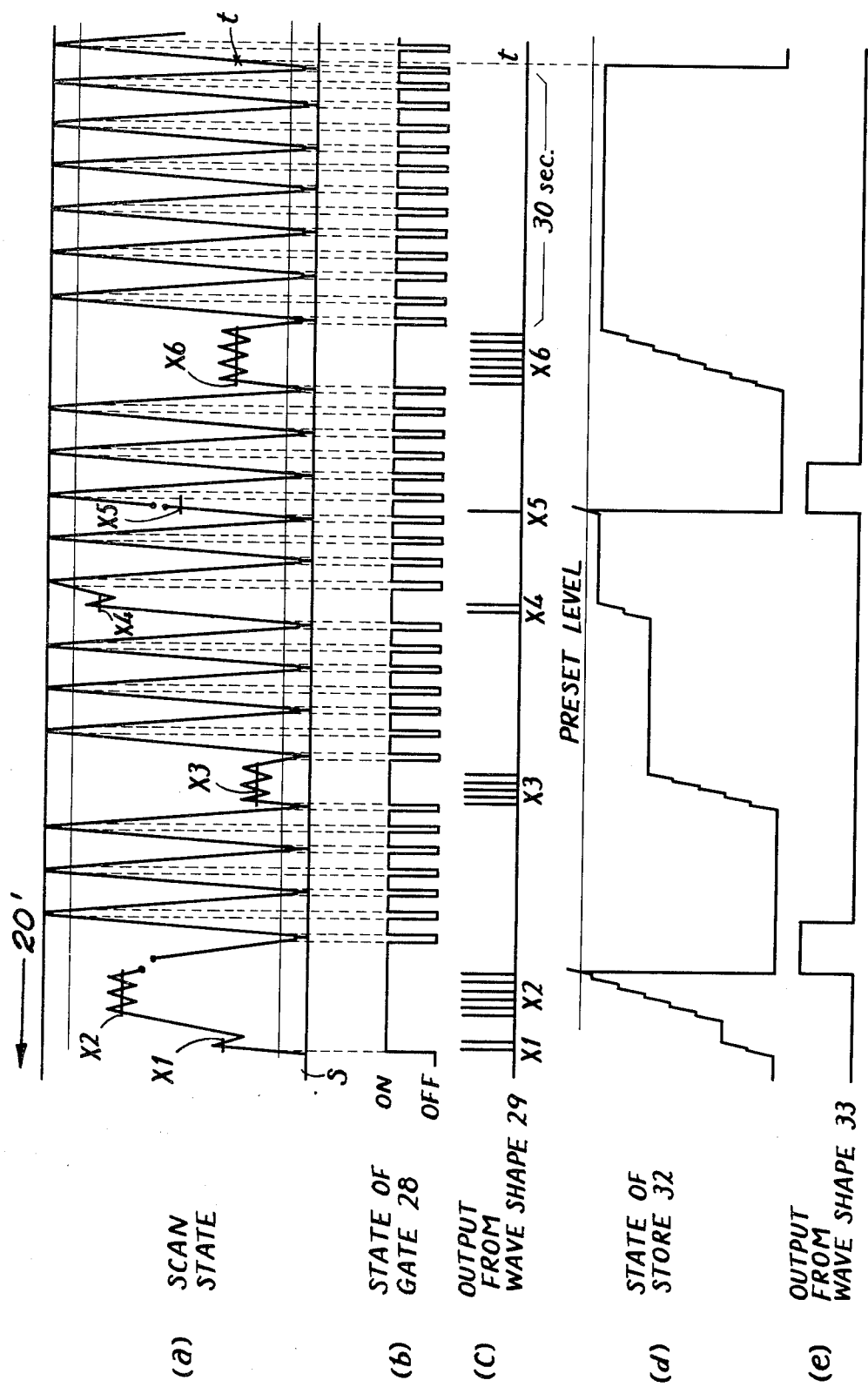
FIG. 6 shows waveforms of electrical signals at various portions in the FIG. 5 embodiment for use in explanation of the operation of the FIG. 5 embodiment.

More detailed description will be made of the operation of the inventive apparatus with reference to FIG. 6, which shows waveforms of electrical signals at various portions in the FIG. 5 embodiment. In operation, assume that the textile sheet S is transferred in the arrow direction 20' as shown in FIG. 6(a) and consider a case where a few defects X1 through X6 exists in the textile sheet. It may be appreciated that in such a situation the detecting device 2 and thus the scanning frame 1 is provided fixedly in the width direction of the textile sheet in the vicinity of the weaving line of the weaving machine, as shown in FIG. 1.

When the detecting device 2 starts to scan the textile sheet from the left end position toward the right end, position the timing switch 27 is turned on after a small delay time selected to disable the detecting operation for the edge portion of the textile sheet S. Accordingly, the gate circuit 28 is enabled or opened. If and when the detecting device 2 detects a first defect X1, a defect detected signal is obtained from the photodetector 6 and thus from the amplifier. Since the gate circuit 28 has been enabled or opened at that time, the defect detected signal is allowed to pass through the gate circuit 28 to trigger the wave shaping circuit 29. Therefore, a pulse output as shown in FIG. 6(c) is obtained from the wave shaping circuit 29. Accordingly, the relay circuit 30 is operable to enable the motor reverse control circuit 31, thereby to rotate the motor 17 in the reverse direction. As a result, the detecting device 2 is caused to convert the moving direction toward the left end, without reaching the right end. The output signal from the wave shaping circuit 29 associated with the detect detected signal is stored in the store circuit 32 by the quantity of electric charge commensurate with one defect detected signal, as shown in FIG. 6(d).

The detecting device 2 when moving in the reverse direction as described above, crosses again the same defect X1, so that another defect detected signal is obtained from the photodetector 6. At that time the gate circuit 28 remains enabled or opened. Accordingly, the second output signal associated with the second detected signal is obtained from the wave shaping circuit 29. Therefore, the motor 17 is again caused to reverse the rotational direction thereof and the detecting device 2 is again moved toward the right end. The store circuit 32 accumulates the quantity of electric charge commensurate with the second detected signal. May be appreciated that the detecting device 2 has effected a fractional scanning operation each time the detecting device 2 detects the defect X1.

The detecting device 2 as reverse controlled as described above comes to cross or scan another defect X2. At that time, the gate circuit 28 has been enabled or opened, since the detecting device 2 has not yet reached the right extremity. Therefore, the defect detected signal obtained from the photodetector 6 serves to trigger the wave shaping circuit 29. Thus, the third output signal associated with the third defect detected signal is obtained from the wave shaping circuit 29. Accordingly, the motor 17 is again caused to reverse the rotational direction thereof, and the store circuit 32 accumulates the quantity of electric charge commensurate with the third defect detected signal, with the result that the store circuit 32 stores the total quantity of electric charge commensurate with three defect detected signals.

The detecting device 2 continuously makes fractional repetitive back and forth scanning operation centering on the defect X2, so that consecutive four to eight defect detected signals are provided. Therefore, store circuit 32 stores the total quantity of electric charge commensurate with eight detected signals, and the potential of the stored charge exceeds a predetermined potential level, with the result that a threshold level detected signal is obtained from the store circuit 32. Accordingly, the wave shaping circuit 33 is triggered, thereby to provide a single pulse signal at this movement, as shown in FIG. 6(e). The output from the wave shaping circuit 33 is applied to the relay circuit 34. As a result, the display 35 is enabled to display detection of an appreciable defect and the weaving machine stop control circuit 36 is enabled to control the weaving machine to be stopped. It should be appreciated that the display indicates that an appreciable defect extending in the warp direction has been detected. On the other hand, the output from the store circuit 32 is applied through TR7, TR8 and TR9 to the discharge circuit 37. Accordingly, the discharge circuit 37 generates a discharging signal, which is applied to the store circuit 32 to discharge the stored charge therein. As a result, the store circuit 32 is discharged at this time and the stored charge returns to zero as shown in FIG. 6(d).

After the defect X2 is detected and the weaving machine is stopped, the textile sheet S is remedied of the defect and the scanning operation by the detecting device 2 is restarted toward the left end. Thus the normal full width scanning operation is continued throughout the width of the textile sheet. Unless any defect exists throughout the full width of the textile sheet S to be scanned by the detecting device 2, the detecting device 2 reaches the left extremity of the textile sheet, where the timing switch 27 is turned on. Accordingly, the gate circuit 28 is turned on for a time period when the end portion of the textile sheet S is scanned by the detecting device 2. When the timing switch 27 is turned on, the gate circuit 28 is opened and the reverse control signal circuit 38 is triggered. Therefore, the reverse control signal circuit 38 provides a reverse control signal at the timing when the timing switch 27 is turned on. Accordingly, the relay circuit 30 becomes operable to convert the rotational direction of the motor 17. Accordingly, the detecting device 2 is caused to scan the textile sheet 2 in the rightward direction. Thus, unless any defect is detected, the motr 17 and thus the detecting device 2 is made to convert the direction at the left extremity of the textile sheet S and thereafter is made to convert the direction at the right extremity of the textile sheet S, and so on. In other words, the detecting device 2 is controlled to make repetitive fractional back and forth scanning operations around a detected defect, only insofar as a defect is detected. The gate circuit 28 is enabled or opened only if the detecting device 2 is scanning a predetermined width of the textile sheet excluding the opposite end portions of the sheet, and the gate circuit 28 is disabled or closed when the detecting device 2 scans the end portion of the textile sheet 2.

The detecting device 2 also detects the other defects X3 X4, and X5 in the textile sheet S, as shown in FIG. 6(d), and an output signal is obtained from the store circuit 32 at the time when the defect detected signal is obtained with respect to the defect X5 and accordingly the pulse output signal is obtained from the wave shaping circuit 33, as shown in FIG. 6(e). As a result, the weaving machine is again stopped and the display 35 is enabled to display existence of another appreciable defect. Thereafter, the detecting device 2 is made to restart the normal full width scanning operation.

Thereafter, the detecting device 2 detects the defect X6 of the textile sheet S and accordingly the wave shaping circuit 29 provides seven consecutive pulses in association with the length of the defect X6, as shown in FIG. 6(c). These seven pulses associated with the defect detected signals are cumulatively stored in the store circuit 32. However, if and when a time period of 30 lapses without detection of any further defects since the above described seventh or the last defect detected signal is obtained with respect to the defect X6, a discharge signal is applied from the delay circuit 39 to the discharge circuit 37. Therefore, when the detecting device 2 reaches the point t on the textile sheet S after the lapse of the time period of 30 seconds from the detection of the final or seventh defect detected signal with respect to the defect X6, the discharge circuit 37 is enabled, thereby to discharge the store circuit 32 which has stored cumulatively the quantity of electric charge for the above described seven defect detected signals but has not reached the predetermined potential level to be detected. As a result, any electric charge stored in the store circuit 32 is discharged at the time point t after the lapse of the time period of thirty seconds, so that the stored charge returns to zero. Since the store circuit 32 has not reached the predetermined threshold level at the time of the above described discharging, no output signal is obtained from the store circuit 32 and accordingly no signal is obtained from the wave shaping circuit 33, as shown in FIG. 6(e). In other words, the above described threshold level to be detected by means of the level detector included in the store circuit 32 is selected to determine the range of tolerance for defects in the textile sheet. In the last described example, the defect X6 is not large enough to cause the store circuit 32 to provide a threshold detected output signal, with the result that the weaving machine is not stopped and the display 35 is not enabled.

Figure 5A:
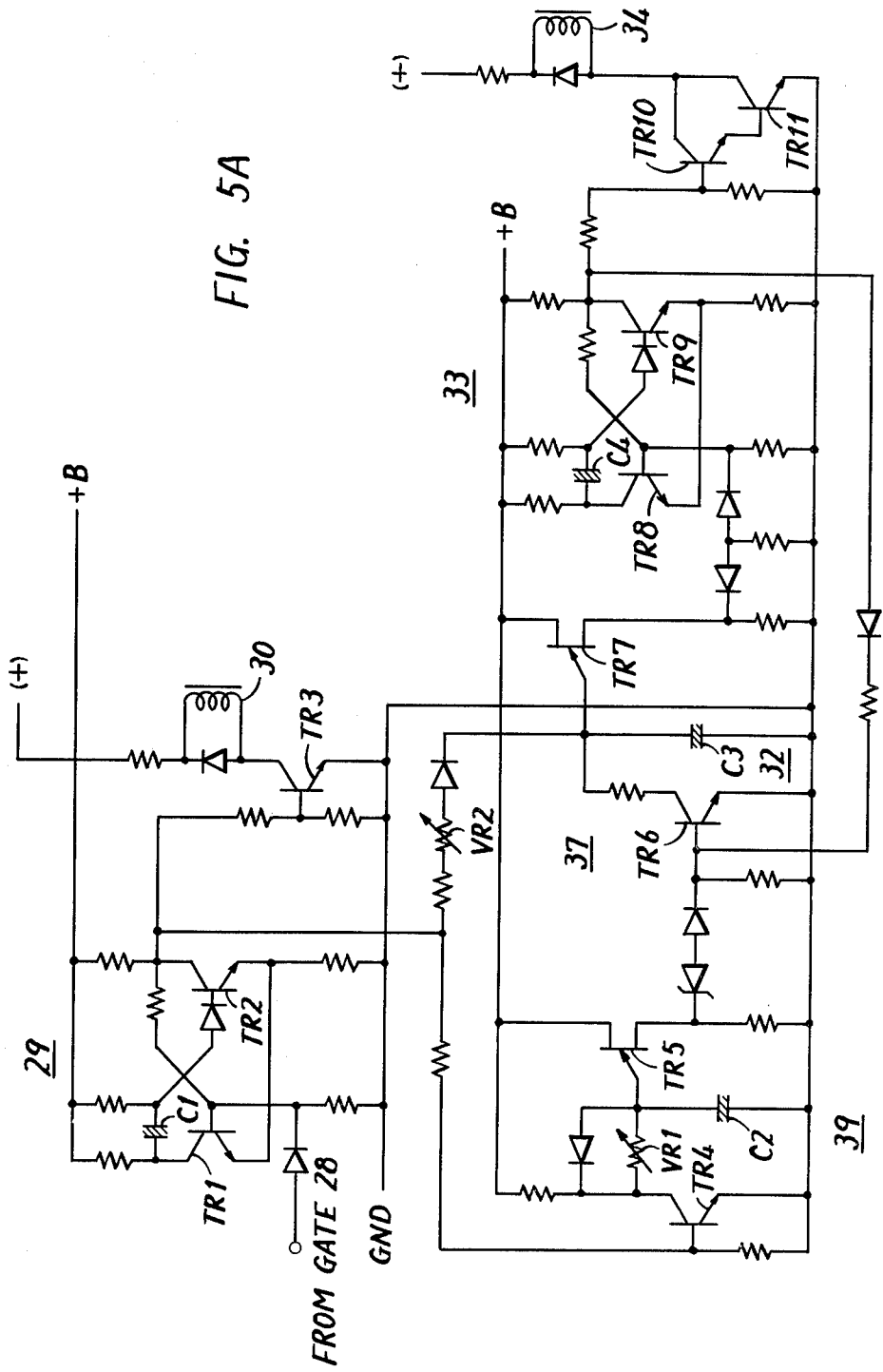
FIG. 5A is a schematic diagram showing in detail a major portion of the FIG. 5 embodiment.

FIG. 5A is a schematic diagram showing in detail a major portion of the FIG. 5 embodiment. Referring now to FIG. 5A, the inventive apparatus will be described in more detail. The above described wave shaping circuit 29 comprises a monostable multivibrator comprising transistors TR1 and TR2 and a capacitor C1. The defect detected signal obtained from the gate circuit 28 is applied through a diode to one transistor TR1, thereby to trigger the monostable multivibrator. Accordingly, a pulse output, as shown in FIG. 6(c), is obtained from the collector of the other transistor TR2. Therefore, a transistor TR3 constituting a driver circuit for a relay 30 is turned on, thereby to energize the relay 30 to reverse the rotation of the motor 17, as described previously.

The pulse output from the wave shaping circuit 29 is applied through a variable resistor VR2 to a capacitor C3 constituting the store circuit 32. The variable resistor VR2 sets the time constant of the charging of the capacitor C3 as charged with the above described pulse output.

The defect detected pulse obtained from the pulse shaping circuit 29 is applied to the delay circuit 39 comprising a transistor TR4, a variable resistor VR1, a capacitor C2 and a unijunction transistor (or a double base diode) TR5. The transistor TR4 is turned on with the pulse, so that the capacitor C2 starts to be discharged through the variable resistor VR1. The variable resistor VR1 adjusts the time constant of the discharging of the capacitor C2 and thus the delay time achieved by this delay circuit 39, for example the above described 30 seconds. When the capacitor C2 is discharged so that a delay time as set by the variable resistor VR1 lapses, the unijunction transistor TR5 becomes conductive. Therefore, a transistor TR6 constituting the discharging circuit 37 is turned on after the lapse of the above described delay time, with the result that the capacitor C3, starts to be discharged through the transistor TR6. Thus, the capacitor C3, constituting the store circuit 32, is prevented from being charged to exceed the predetermined threshold level, if and when the defect is not long enough to charge the capacitor C3 to that level.

Assuming that the defect is appreciably long and a number of defect detected pulses are consecutively obtained from the wave shaping circuit 29 before the lapse of the above described delay time by the delay circuit 39, as for example in the case of the defect X2, the capacitor C3 is charged with these defect detected pulses stepwise through the variable resistor VR2, with the result that the predetermined threshold level is exceeded by the stored charge potential, as shown in FIG. 6(d). Then the unijunction transistor TR7 is turned on and accordingly the wave shaping circuit 33, comprising a monostable multivibrator implemented by transistors TR8 and TR9 and a capacitor C4, is triggered.

As a result, it follows that a pulse output signal as shown in FIG. 6(e) is obtained from the wave shaping circuit 33, and transistors TR10 and TR11 constituting a driver circuit for a relay 34 are turned on. Accordingly, the relay 34 is energized to stop the weaving machine, for example. Simultaneously, the pulse output signal from the circuit 33 is applied to the base of the transistor TR6 of the above described discharge circuit 37, thereby to discharge the capacitor C3 of the store circuit 32. Thus, the capacitor C3 is returned to the initial state, so that it may be charged with any subsequent defect detected pulses.

At the same time as the relay 34 is energized by the pulse output obtained from the wave shaping circuit 33 as shown in FIG. 6(e), the display 35 is also enabled to display existence of an appreciable defect, as described previously.

According to the above described embodiment of the present invention, the various electronics, including amplifiers, can be implemented in the form of an integrated circuit in the light of the art of recent development of the electronics, and a detecting head combined with amplifiers can be implemented in a small size, so that a mechanical scanning structure for the detecting head can be made simple, inasmuch as an electrical cord can be dispensed with. The embodiment shown is further structured such that defect detected signals, as obtained from the amplifier internally of the detecting device, are withdrawn in the form of pulses through the guide rails, with the result that a noise that could occur between the contact rollers and the guide rails does not cause any malfunction in the inventive apparatus. In addition, the above described fractional, repetitive, back and forth scanning operation serves to eliminate any malfunction in the inventive apparatus. The consecutive defect detected signals obtained by such fractional repetitive scanning operation can be used for signal processing, such as accumulation of the consecutive signals and threshold detection of the accumulated value, and the like and the control signal thus obtained can be used for displaying and recording purposes, and for stop controlling of the weaving machine.

In the above described embodiment only the detecting device for detecting a warp directional defect was described. However, it should be pointed out that the present invention is also applicable to the detection of a woof directional defect in a textile sheet. As well known to those skilled in the art, various apparatus for detecting a woof directional defect have been developed and put into practical use. However, if more severe detection of a woof directional defect is necessary, a woof defect detecting apparatus adapted for illuminating the sheet surface with an elongated light beam extending in the woof direction may be advantageously combined with the inventive apparatus. More specifically, the inventive apparatus may advantageously incorporate a scheme wherein upon detection of a woof directional defect, the full width scanning operation is discontinued and instead the fractional repetitive scanning operation is adapted to be effected in the warp direction, with the result that substantially the same advantages can be brought to the detection of woof directional defects. If the present invention is employed both to warp and woof directionsl defect detecting apparatuses simultaneously, simultaneous detection of a defect by means of both apparatuses makes it possible to detect a defect in a given area. In case of a woof directional defect extending throughout the full width of the textile sheet, the defect could be detected even if the detecting device is fixed on the width line of the textile sheet.

Although in the above described embodiment, a detector of a photoelectric, coaxial reflection type is employed, alternatively, any other detectors, such as a permeation type can be used. The inventive apparatus can further be utilized for the purpose of defect detection in any type of sheet like material other than a textile sheet.

The above described embodiment comprises guide rails 12, 13 and 14 and the contact rollers 9, 10 and 11 in sliding electrical contact therewith for the purpose of achieving transmission of electricity form a power supply and also the signals between the control circuit portion and the detecting device 2. Such implementation is satisfactory, as far as easy operation and maintenance of the apparatus and appearance thereof are concerned. Nevertheless, as the scanning speed of the detecting device 2 is increased, the contact between the contact rollers 9, 10 and 11 and the guide rails 12, 13 and 14 is liable to become poor. Hence noise is liable to be caused therefrom and a defect detected signal is liable to be adversely affected by such noise. In addition, the contact rollers and the guide rails are liable to be contaminated with various dust, which is also liable to cause noise.

Figure 7A:
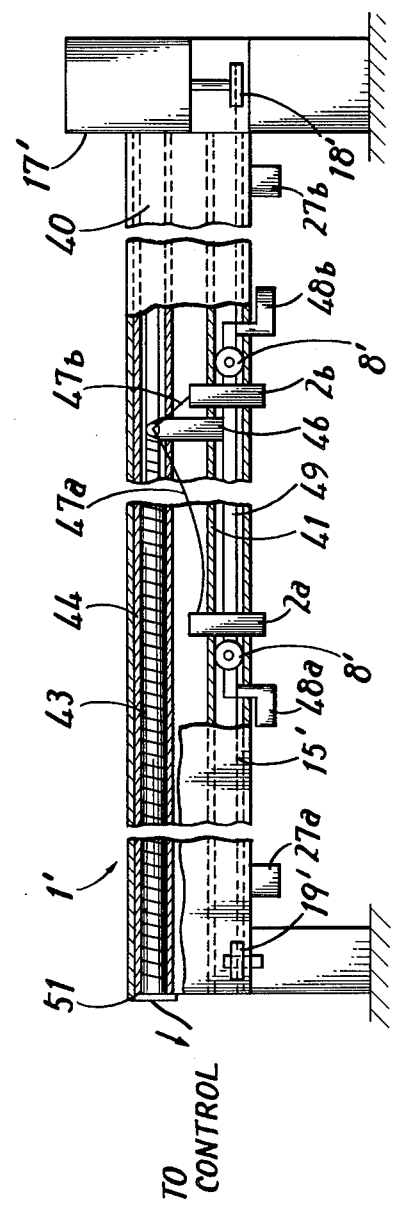
FIG. 7A is an elevational view, partially in section, of another embodiment of a scanning frame for use in the present invention.
Figure 7B:
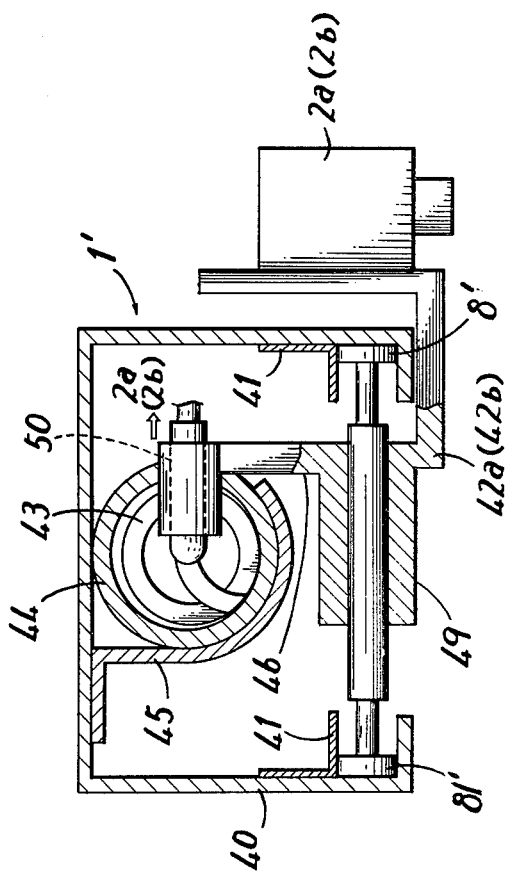
FIG. 7B is a left side view of the FIG. 7A embodiment.

The embodiment shown in FIGS. 7A and 7B has an improved scanning frame for eliminating the above described shortcomings. Referring to FIGS. 7A and 7B, the scanning frame 1' is arranged to extend throughout the full width of the textile sheet (not shown) in the width direction. The outer wall 40 of the scanning frame 1' comprises a tube of C shaped cross-section, and a driving motor 17' is provided at one end of the frame for drivingly moving detecting devices 2a and 2b, as shown in FIG. 7A. The motor 17' is of a type forwardly and reversely controllable and comprises a drive pulley 18' mounted on the shaft thereof. A driven pulley 19' is rotatably provided at the other end of the above described scanning frame 1' and on the outer wall 40. An endless wire 15' is suspended between the drive pulley 18' and the driven pulley 19'. A carriage 49, as long as a half of the full width of the textile sheet or the scanning width, is fixed to the endless wire 15', so that the carriage 49 is moved as the endless wire 15 is rotated. Two pair of rollers 8', 81' and 8', 81' are rotatably provided at the opposite ends of the carriage 49. As best seen in FIG. 7B, angles 41 and 41 are provided on the inside surface of the vertical walls of the outer wall 40 spaced apart from the lower flange portions to form grooves at both sides of the outer wall 40 between the opposing angle 41 and the lower flange portion. The rollers 81, 81' of the carriage 49 are adapted to be received slidably within the above described grooves defined by the angle 41 and the lower flange portion, thereby to achieve a stabilized travel of the carriage 49 along the scanning frame 1'.

As best seen in FIG. 7B, an arm 42a is provided at one end of the carriage 49 and an arm 42b is provided at the other end of the carriage 49, each extending toward the front side of the weaving machine, i.e. rightward as viewed in FIG. 7B. The detecting device 2a is provided at the free end of the one arm 42a and the detecting device 2b is provided at the free end of the other arm 42b. These two detecting devices 2a and 2b each comprise a combination of a light source and a photodetector for receiving a light beam reflected from the surface of a given sheet like material. According to the embodiment shown, these two detecting devices are each adapted to scan only a half of the full width of the textile sheet and together the full scanning width. Accordingly, the width of the carriage 49 and thus the distance between these two detecting devices 2a and 2b is selected to be a half of the full scanning width of the textile sheet.

Referring to FIG. 7A, photoelectric switches 27a and 27b, serving as the above described timing switch, are provided at the lower side of the opposite ends of the outer wall 40 so as to correspond to the opposite ends of the range to be detected of the sheet like material. The above described carriage 49 is provided with shutters 48a and 48b at the opposite ends of the carriage 49 for the purpose of screening the light beam from the photoelectric switches 27a and 27b. Therefore, when the detecting devices 2a and 2b reach the corresponding end of the sheet like material, the corresponding shutter 48a or 48b screens the light beam of the photoelectric switch 27a or 27b, respectively, with the result that a pulse signal is obtained from the corresponding photoelectric switch 27a or 27b, respectively. This pulse signal is applied to a control, not shown, by way of a reverse control signal to the motor 17'. As a result, the motor 17 is caused to reverse the rotational direction thereof each time the above described pulse signal is generated and accordingly the carriage 49 repeats a reciprocating movement. Thus, the detecting devices 2a and 2b are caused to repeatedly scan the textile sheet such that each covers only a half of the full scanning width of the textile sheet.

The above described C-shaped wall 40 is further provided with a cylindrical guide 44 at the inside of the top plate portion extending in the longitudinal direction thereof, i.e. in the width direction of the textile sheet throughtout the full width such that the guide 44 is supported by a plurality of fixing members 46. The cylindrical guide 44 is formed of a groove at the front side surface thereof extending the length associated with the fixing members 46 to be described subsequently. This guide 44 is utilized for receiving a spiral coil of shielded wire 43 for the transmission of the electricity from the power supply and a defect detected signal between the control (not shown) and the above described detecting devices 2a and 2b. The length of the wire 43 received inside the guide 44 may be as long as a half of the scanning width, if two detecting devices 2a and 2b are employed, as shown in the figure, in which case transmission of the electric power and the signals concerned is performed while the wire 43 is extended two times in length at the maximum. More specifically, if and when the detecting device 2a is in the left most position of the sheet like material and the detecting device 2b is in the middle portion of the sheet like material, the wire 43 is in the most contracted form of the spiral coil, in which case the wire is of the length from the left end portion 51 of the scanning frame 1' to the detecting device 2b.

One end of the wire 43 is fixed to one end of the guide 44 and is connected to the control, not shown. The carriage 49 is provided with a fixture 46 extending substantially upright and securing the other end of the wire 43. The upper end 50 of the fixture 46 is structured to be matably inserted into the groove formed in the guide 44. The other end of the wire 43 is connected to one of the ends of two straight shielded wires 47a and 47b for connection to the above described detecting devices 2a and 2b. The other respective ends of these two straight shielded wires 47a and 47b are connected to the detecting devices 2a and 2b, respectively. Thus, the detecting devices 2a and 2b and the control, not shown, are connected by means of the spiral coil wire 43 and the straight shielded wires 47a and 47b. Accordingly, as the detecting devices 2a and 2b scan the sheet like material, the spiral coil wire 43 extends or contracts within the guide 44 following the moving carriage 49.

According to the embodiment shown in FIGS. 7a, 7b a spiral shielded wire is employed by way of the wire 43. Therefore, the wire and thus the wire guide 44 can be housed in the scanning frame 1'. As a result, the apparatus can be made simple in structure. Furthermore, maintenence of the weaving meachine, particularly rectification of warp snapping, a wooven flaw and the like can be achieved with ease without any obstruction by provision of the present inventive apparatus. In addition, since a shielded wire is used, as different from the guide rails in this FIG. 2A embodiment, the embodiment is immune to noise induced by mechanical vibration of the weaving machine and by the wire itself, with the result that a defect detected signal can be obtained with higher accuracy. Although in this embodiment two detectors are employed, alternatively three or more detectors may be used to cover the full scanning width of the textile sheet.

According to this scanning system, the light source and the photodetector are kept such that the axes of the light beams from and toward them are in the same angle with respect to the surface of the sheet like material, and therefore the reflected light beam as received from the abnormality on the sheet like material is received by the photodetector always in the same direction. However, this is disadvantageous in that the abnormalities are generally irregular in terms of three-dimension, which makes uniform detection of such irregular abnormalities difficult with the above described scanning system. In employing the above described scanning system, the photodetector may be adapted to scan the sheet like material in the width direction, while the light source is adapted to illuminate uniformly the sheet like material throughout the full width thereof. According to this approach, however, since a uniform light flux is adapted to impinge upon the sheet like material throughout the full width thereof, as compared with the detecting device wherein a combination of a light source and a photodetector is adapted to scan the sheet like material in the width direction, the ratio of the light beam reflected from an abnormality to the light beam reflected from the normal area of the sheet like material, i.e. a signal to noise ratio, is small, resulting in possible failure in detection of abnormalities.

Figure 8:
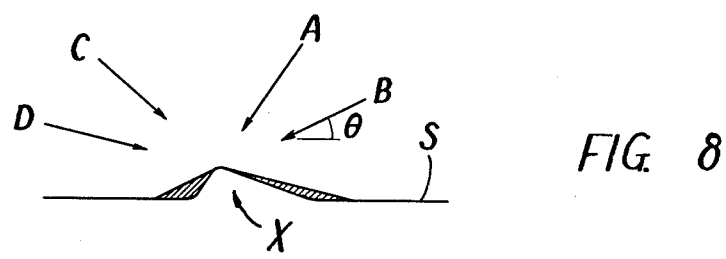
FIG. 8 is an enlarged sectional view of an abnormality in the textile sheet for use in explaining the background and the principle of another preferred embodiment of the detecting apparatus 2 of the present invention.

This will be described in more detail with particular reference to FIG. 8, which shows an enlarged sectional view of an abnormality in the textile sheet. Let it be assumed that a convex abnormality X exists on the surface of the sheet like material S, as shown in the figure. In such a situation, in a case where the sheet like material S is illuminated by the light beams such as A or B directed from the right upper side, the signal-to-noise ratio of the signal obtainable with respect to the light beam B is larger than the signal-to-noise ratio of the signal obtainable with respect to the light beam A. On the contrary, in the case where the light beam, such as C or D, coming from the left upper direction, the signal-to-noise ratio of the signal obtainable with respect to the light beam D is larger than the signal-to-noise ratio of the signal obtainable with respect to the light beam C. It is appreciated that this is caused by the irregularity of the abnormality with respect to the incident direction of the light beam. In other words, the angle of the incident light beam with respect to the sheet like material S, in which the defect detected signal of the maximum signal-to-noise ratio is different, is dependent on various abnormalities. According to the conventional approach, however, no consideration has been given to impingement of the light beam on the sheet like material at an adjustable angle and the scanning operation has been made of the sheet like material at a predetermined fixed angle of the optical axes of the light beams from the light source and toward the photodetector. Hence, malfunction was liable to occur to detecting irregular abnormalities on the sheet like material with the conventional apparatus. Nevertheless, as a matter of practice, there could be various types of abnormalities and such malfunction is not permissible.

FIG. 9 is a diagrammatic view of a further preferred embodiment of the detecting apparatus adapted for eliminating the above described disadvantages. Referring to FIG. 9, the detecting device 2' constitutes an essential feature of the embodiment shown, wherein a photodetector 6' is provided vertically above the portion to be detected of the sheet like material S, and a plurality of (two in the embodiment shown) light sources are provided at each of the left and right sides, as at 3a and 3b, and 3c and 3d, with the photodetector 6' in the center, as seen in FIG. 9. The optical system implemented by these light sources and the photodetector is structured such that the image of the portion to be detected on the sheet like material is obtained in the focus distance of the lens 6a provided in front of the photodetector 6'. It is appreciated that the light sources are provided to achieve different angles of the light beam axes incident upon the portion being detected of the sheet like material and hence the number of the light sources and the angle of the light beam axes may be selected as desired.

In operation, if and when the detecting device 2' reaches one end of the sheet like material S, the above described screen plate 48 screens the light beam toward the photoelectric switch 27a to provide a pulse signal. Referring to FIG. 10, the pulse signal obtained from the photoelectric switch 27a is applied to the counter 52 and to the reverse control signal generator 38. Accordingly, a reverse control signal is supplied from the reverse control signal generator 38 to the relay 30 and thus to the motor reverse control circuit 31. Therefore, the motor 17" starts to reverse the rotation thereof and the detecting device 2' is moved toward the opposite end of the sheet like material S. If and when the detecting device 2' reaches the opposite end of the sheet like material S, then the above described screen plate 48b screens the light beam toward the photoelectric switch 27b, thereby to provide a pulse signal. The pulse signal obtained from the photoelectric switch 27b is also applied to the counter 52 and the reverse control signal generator 38. Thus, the detecting device 2 repeats reciprocating movement in the width direction of the sheet like material S throughout the full width thereof.

The counter 52 comprises an N-binary counter or N-positional ring counter which is responsive to the above described pulse signal to be shifted or stepped, thereby to provide the count value to a signal distributer 53. The signal distributer 53 preferably comprises a decoder matrix configuration and is responsive to the output from the said counter 52 to provide an output therefrom. The output from the signal distributer 53 is utilized to enable or energize the corresponding light sources 3a, 3b, 3c and 3d. Accordingly, these light sources, 3a, 3b, 3c and 3d are selectively energized, one by one, as the count value in the counter proceeds each time the motor 17' is caused to reverse in the rotation thereof, i.e. as the number of scanning operations by the detecting device 2' increases, with the result that the light sources 3a through 3d are sequentially switched. As a result, the surface of the sheet like material S is scanned by the detecting device 2' with an incidental light beam the angle of which is variable as the scanning operation is repeated.

The photodetector 6' receives the light beam reflected from the surface of the sheet like material S to convert the intensity thereof into an electric signal, which is then applied to a subsequent amplifier. When an abnormality on the sheet like material S is detected, a pulse output signal is obtained from the photodetector 6'. The defect detected pulse signal is applied through the gate circuit 28 to the wave shaping circuit 29 shown in FIG. 5. The defect detected signal from the wave shaping circuit 29 is applied to the store circuit 32. As described previously, the store circuit 32 serves to provide a control signal each time it receives the defect detected signal, or each time it receives a predetermined number of defect detected signals, thereby to control the weaving machine to stop transfer of the sheet like material S, stamp the sheet like material S with a mark indicating detection of an abnormality, provide an external control signal, and so on.

According to the third embodiment, irregular abnormalities having various three-dimensional geometry existing on the surface of the sheet like material can be homogeneously detected.

In this embodiment, the photodetector is fixed at a given angle with respect to the surface of the sheet like material, while one or more light sources are provided at each of the left and right sides of the photodetectors at given oblique angles, and these light sources are switched on in turn while the scanning operation is repeated. Alternatively, however, a photodetector may be adapted to be variably inclined with respect to the surface of the sheet like material in synchronism with a change in illumination by the light source, such that a photodetector is slightly inclined leftward when the incidental light beam is directed from the right side, while the photodetector is inclined slightly rightward when the incidental light beam is directed from the left side. Alternatively, a plurality of photodetectors are provided at both the right and left sides so as to be inclined with respect to the surface of the sheet like material, such that when the incidental light beam is directed from the right side light source the photodetector which is inclined leftward is enabled, while when the incidental light beam is directed from the left side light source, the photodetector which is inclined rightward is enabled. For the purpose of the present invention, any other modifications may be employed. For example, alternatively of changing the angle of the incidental light beam in accordance with the count value of the scanning operations, the angle of the incidental light beam may be changed at every predetermined time period.

Although this invention has been described and illustrated in detail, it is to be clearly understood that the same is by way of illustration and example only and is not to be taken by way of limitation, the spirit and scope of this invention being limited only by the terms of the appended claims.

What is claimed is:

1. An apparatus for detecting a defect in a sheet like material, comprising;
    means provided opposite to the surface of said sheet like material for detecting a defect on said sheet like material,
    means for causing relative movement of said defect detecting means with respect to said sheet like material in a given direction of said sheet like material for scanning said sheet like material by said defect detecting means throughout a first relatively large distance in said given direction,
    means responsive to a defect detected output from said defect detecting means for controlling said relative movement causing means for scanning said screen like material by said defect detecting means throughout a second relatively small distance in said given direction including the detected defect,
    said relative movement causing means comprises guide means provided in said given direction of said sheet like material for slidably supporting said defect detecting means for movement in said given direction of said sheet like material,
    means for driving said defect detecting means along said guide means,
    said relative movement causing means comprises a flexible electric wire provided in said guide means for electrical connection to said defect detecting means,
    wire cover means in said guide means for covering said flexible electric wire, and
    said electric wire comprises a flexible spiral coil wire.

2. An apparatus for detecting a defect in a sheet like material in accordance with claim 1, wherein said defect detecting means comprises a plurality of defect detecting means provided spaced apart from each other in said given direction, and said wire cover means is adapted to cover said electric wire between said plurality of defect detecting means.

3. An apparatus for detecting a defect in a sheet like material in accordance with claim 2, wherein each of said plurality of defect detecting means is adapted to scan the corresponding fraction of said first relatively large distance of said sheet like material.

4. An apparatus for detecting a defect in a sheet like material, comprising;
- means provided opposite to the surface of said sheet like material for detecting a defect on said sheet like material,
- means for causing relative movement of said defect detecting means with respect to said sheet like material in a given direction of said sheet like material for scanning said sheet like material by said defect detecting means throughout a first relatively large distance in said given direction,
- means responsive to a defect detected output from said defect detecting means for controlling said relative movement causing means for scanning said sheet like material by said defect detecting means throughout a second relatively small distance in said given direction including the detected defect,
- said defect detecting means comprises a light source for directing a light beam toward the surface of said sheet like material and a photodetector for receiving a light beam coming from the surface of said sheet like material, and
- means operatively coupled to said defect detecting means for changing the light beam axes of said defect detecting means with respect to the surface of said sheet like material in accordance with the progress of said scanning operation of said defect detecting means.

5. An apparatus for detecting a defect in a sheet like material in accordance with claim 4, wherein said defect detecting means comprises a single photodetector, and at least one light source obliquely provided with respect to the surface of said sheet like material at each of both sides of said photodetector, and said angle changing means comprises means for sequentially enabling said light sources in accordance with the progress of the scanning operation.

6. An apparatus for detecting a defect in a sheet like material in accordance with claim 14, wherein said relative movement causing means further comprises means for generating a timing signal whenever a predetermined scanning directional position of said sheet like material is scanned by said defect detecting means, and which further comprises means responsive to said timing signal for controlling said angle changing means.

7. An apparatus for detecting a defect in a sheet like material in accordance with claim 4, which further comprises timing means for detecting the progress of the scanning operation for controlling said angle changing means.

8. An apparatus for detecting a defect in a sheet like material, comprising;
- means provided opposite to the surface of said sheet like material for detecting a defect on said sheet like material,
- means for causing relative movement of said defect detecting means with respect to said sheet like material in a given direction of said sheet like material for scanning said sheet like material by said defect detecting means throughout a first relatively large distance in said given direction,
- means responsive to a defect detected output from said defect detecting means for controlling said relative movement causing means for scanning said sheet like material by said defect detecting means throughout a second relatively small distance in said given direction including the detected defect,
- said defect detecting means including light source means for directing a light beam toward the surface of said sheet like material and photodetector means for receiving a light beam transmitted through said sheet like material, and
- means for changing the light beam axes of said defect detecting means with respect to the surface of said sheet like material in accordance with the progress of the scanning operation by said defect detecting means.

* * * * *

UNITED STATES PATENT AND TRADEMARK OFFICE
CERTIFICATE OF CORRECTION

PATENT NO. : 4,131,803

DATED : December 26, 1978

INVENTOR(S) : Shigeru Takematsu et al.

It is certified that error appears in the above-identified patent and that said Letters Patent are hereby corrected as shown below:

Col. 5, line 21, "meachine" should be --machine--;

Col. 7, line 47, "May" should be --It may--;

Col. 8, line 47, "motr" should be --motor--;

Col. 8, line 61, after "X3" insert --,--;

Col. 11, line 22, "directionsl" should be --directional--;

Col. 11, line 39, "form" should be --from--;

Col. 12, line 11, "81" should be --8'--;

Col. 13, line 40, "meachine" should be --machine--;

Col. 14, line 66, "2'" should be --2"--;

Col. 15, line 9, "2'" should be --2"--;

UNITED STATES PATENT AND TRADEMARK OFFICE
CERTIFICATE OF CORRECTION

PATENT NO. : 4,131,803

DATED : December 26, 1978

INVENTOR(S) : Shigeru Takematsu et al.

It is certified that error appears in the above-identified patent and that said Letters Patent are hereby corrected as shown below:

Col. 15, line 11, "2'" should be --2"--;

Col. 15, line 17, "2" should be --2"--;

Col. 15, line 32, "17'" should be --17"--;

Col. 15, line 34, "2'" should be --2"--;

Col. 15, line 37, "2'" should be --2"--.

Signed and Sealed this

Twenty-second Day of May 1979

[SEAL]

Attest:

RUTH C. MASON
Attesting Officer

DONALD W. BANNER
Commissioner of Patents and Trademarks